United States Patent [19]

Rothman et al.

[11] 4,124,705

[45] Nov. 7, 1978

[54] AGENT FOR INTRAVASCULAR ADMINISTRATION

[75] Inventors: Ulf S. E. Rothman, Höllviksnäs; Bernt J. Lindberg, Upsala, both of Sweden

[73] Assignee: Pharmacia Aktiebolag, Upsala, Sweden

[21] Appl. No.: 583,217

[22] Filed: Jun. 2, 1975

[30] Foreign Application Priority Data

Jun. 6, 1974 [SE] Sweden ............................... 7407462

[51] Int. Cl.$^2$ .................... A61K 31/715; A61K 29/02
[52] U.S. Cl. ....................................... 424/180; 424/4; 536/1; 536/120
[58] Field of Search ....................... 424/180, 9, 1, 4, 5; 536/1, 120

[56] References Cited

U.S. PATENT DOCUMENTS 3,275,576   9/1966   Flodin et al. .......................... 536/120

OTHER PUBLICATIONS

Lowe and Dean, "Affinity Chromatography", Wiley and Sons, N.Y., 1974, pp. 201 and 249.

Primary Examiner—Natalie Trousof
Assistant Examiner—Cary Owens
Attorney, Agent, or Firm—Fred Philpitt

[57] ABSTRACT

The present invention relates to an agent for intravascular administration, said agent consisting of a suspension of minute polysaccharide particles having a size such that subsequent to being administered intravascularly, they block the finer blood vessels of the body and a diagnostic agent.

29 Claims, No Drawings

AGENT FOR INTRAVASCULAR ADMINISTRATION

The present invention relates to an agent for intravascular administration, said agent consisting of or containing a suspension of minute particles having a size such that subsequent to being administered intravascularly they block the finer blood vessels of the body.

It is previously known to use suspensions of minute particles of different materials for intravascular administration to animals and humans for diagnostic or therapeutic purposes, for example. Examples of such particles are those produced from protein, such as serum albumin. Such particles are found described in the German Offenlegungschrift No. Specification 1,916,704, for example. Such tests have also been carried out with particles based on polysaccharides or waxes. Synthetic polymer particles such as polystyrene, and also minute particles of inorganic material have also been used experimentally to block the blood vessels of animals.

The particles previously tested in this regard are encumbered with a number of disadvantages. One such disadvantage resides in the fact that some particles do not decompose or decompose too slowly in the blood vessels and remain more or less permanently in said vessels. They can give rise to small thromboses which do not regress, even should the particles be subsequently dissolved or decomposed and leave the blood vessel in question, which obviously leads to serious consequences. Another disadvantage resides in the fact that most of the previously tested particles, for example albumin-based particles, exhibit poor suspension stability and are prone to sedimentation and/or conglomeration (e.g. owing to the high specific weight and/or the adhesiveness of the particles) rendering it necessary to subject the suspension to ultrasonic treatment in order to prevent this from happening. However, the stability of such earlier particle suspensions treated ultrasonically is very poor and the suspension must be used as soon as possible after said treatment. The stability of the particles (for example the albumin particles) is often so poor as to render it necessary to store said particles in freeze dried condition, the durability of the particles being, nevertheless, still limited. Some particles are unable to withstand variations in temperature and cannot be sterilized by heat treatment. The previously tested particles have either not been dissolvable or degradable in blood plasma, or have been dissolvable or degradable only in an irregular and non-reproducable manner, or have been changed in this regard during storage, which presents considerable disadvantages and risks.

It has been surprisingly discovered that the aforementioned disadvantages encountered with the previously used particles can be eliminated by means of the present invention.

More specificly, the present invention relates to an agent for intravascular administration, preferably for use in conjunction with the intravascular administration of a diagnostic agent or a therapeutic agent in solution or in suspension, in a vessel (preferably a blood vessel) located in or leading to a specific portion of the body, said agent consisting of or containing a suspension of minute particles which comprise a polysaccharide built up of glucose units or a physiologically acceptable derivative of said polysaccharide in a physiologically acceptable aqueous liquid, said particles having a size such that, subsequent to being administered intravascularly, they block the finer vessels located in or leading to said body portion.

The agent according to the invention is characterized in that the aforementioned particles comprise a water-insoluble but hydrophilic, swellable (i.e. swellable in water), three-dimensional network of molecules of the polysaccharide or of the derivative thereof cross-linked by means of bridges having bonds of a covalent nature, which network can be broken up by $\alpha$-amylase in blood plasma into water-soluble fragments, either directly or subsequent to preceding splitting off of possibly occurring substituents, preferably glucoside-bound and/or ester-bound substituents, in the polysaccharide by the action of an enzyme, preferably glucosidase and/or esterase, in blood plasma.

The polysaccharide which is built up of glucose units and which shall be incorporated (as such or in the form of a physiologically acceptable derivative) in cross-linked form in the particles, shall be capable of being degraded by $\alpha$-amylase into water-soluble fragments, i.e. the polysaccharide shall contain $\alpha$ $(1 \rightarrow 4)$ glucosidic linkages which are hydrolyzable by $\alpha$-amylases. Examples of such polysaccharides include primarily starch and glycogen or dextrins thereof. The starch may be amylose or amylopectin or mixtures thereof. Other glucose-containing polysaccharides which can be hydrolysed by $\alpha$-amylase can also be used, in connection with which said polysaccharides may be synthetic or may be obtained from biological material, for example from microorganisms. It is simplest and cheapest, however, to use starch in the form of amylose or amylopectin or mixtures thereof. Similarly, the physiologically acceptable derivative of the polysaccharide shall be degradable by $\alpha$-amylase directly or subsequent to a preceding splitting-off of substituents under the action of an enzyme in blood plasma, such as for example esterases or glucosidases. Substituents in the polysaccharide may, for example, by hydroxyalkyl groups (which are optionally broken by one or more oxygen atoms), for example lower hydroxyalkyl groups having for example 2–6 carbon atoms such as 2-hydroxyethyl, 2-hydroxypropyl and/or 2,3-dihydroxypropyl, and/or alkyl groups, e.g. lower alkyl groups having 1–6 carbon atoms such as methyl and/or ethyl, and/or substituted alkyl groups, e.g. substituted with carboxyl groups such as carboxy methyl and/or alkanoyl groups, or substituted alkanoyl groups, e.g. lower alkanoyl groups having e.g. 2–6 carbon atoms, such as acetyl, propionyl, 2-hydroxypropanoyl, succinoyl and/or glutaroyl. The reducing end group of the polysaccharide may be unchanged or modified. For example, it may be oxidized or reduced, so that said end of the polysaccharide chain is terminated with a carboxyl group or a primary hydroxyl group. It may, for example, also be present in the form of a glucoside, e.g. with an alcohol such as glycerol.

The cross-linking bridges may be bound to the molecules of the polysaccharide or the derivative thereof over different types of bonds. In accordance with a particularly suitable embodiment of the invention, these bonds are ether bonds. In accordance with a further suitable embodiment of the invention, said bonds are ester bonds, the term ester bonds being used here in its widest significance. Thus, the term also includes for example, carbamic acid ester bonds and thiocarbamic acid ester bonds. Preferably, aliphatic bridge building links are chosen, although said links may also be, for example, aromatic or araliphatic.

The cross-linking bridges may also contain to advantage hydrophilic groups, e.g. hydroxyl groups (e.g. one to six hydroxyl groups in each bridge).

In accordance with the invention, the cross-linked polysaccharide molecules in the practically infinite three-dimensional network may be substituted with other substituents than the cross-linking bridges. For example, these substituents may be one or more of the aforementioned substituents, e.g. hydroxyalkyl, alkyl and/or alkanoyl. As will be readily understood, monofunctionally bound substituents originating from the cross-linking agent may also occur.

In accordance with a particularly suitable and practical embodiment of the invention, the molecules of the polysaccharide or of the derivative thereof are cross-linked by means of bridges which are bound to these molecules over ether bonds, wherein the bridges between the ether bonds may advantageously be straight or branched aliphatic saturated hydrocarbon chains which are substituted by one or more hydroxyl groups (e.g. one to six hydroxyl groups) and which contain 3–30 carbon atoms, preferably 3–20 carbon atoms, such as 3–10 carbon atoms, and which are optionally broken by one or more oxygen atoms (e.g. one to six oxygen atoms). Examples of such ether-bound cross-linking bridges are —CH$_2$ . CH(OH) . CH$_2$— and —CH$_2$ . CH(OH) . CH(OH) . CH$_2$— and —CH$_2$ . CH(OH) . CH$_2$ . O . CH$_2$ . CH(OH) — CH$_2$— and —CH$_2$ . CH(OH) . CH$_2$ . O . (CH$_2$)$_n$ . O . CH$_2$ . CH(OH) . CH$_2$—, where $n$ is an integer, for example an integer from 2 to 4, and

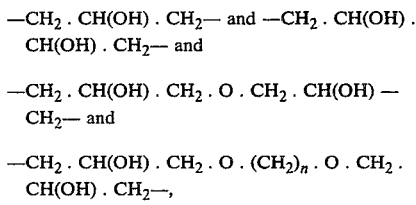

—CH$_2$.CH(OH).CH$_2$.O.$\overset{\overset{\displaystyle CH_3}{|}}{CH}$.CH$_2$.CH$_2$.O.CH$_2$.CH(OH).CH$_2$— and

—CH$_2$ . CH(OH) . CH$_2$ .O.CH$_2$.CH$_2$.O.CH$_2$.CH$_2$.O.CH$_2$.CH(OH).CH$_2$— and —CH$_2$ . CH(OH) . CH$_2$.O.CH$_2$.CH(OH).CH$_2$.O.(CH$_2$)$_n$.O.CH$_2$.CH(OH).CH$_2$.O.CH$_2$.CH(OH).CH$_2$—, where $n$ is an integer, for example an integer from 2 to 4.

In accordance with another embodiment of the invention, the molecules of the polysaccharide or of the derivative thereof are cross-linked by means of bridges which are bound to said molecules over ester bonds which may preferably be carboxylic acid ester bonds, but which may also be carbamic acid ester bonds or thiocarbamic acid ester bonds, the bridges between the ester bonds advantageously being straight or branched aliphatic saturated hydrocarbon chains containing 2–20 carbon atoms, preferably 2–10 carbon atoms such as 2–6 carbon atoms, and being optionally broken by one or more oxygen atoms (e.g. one to six oxygen atoms) and optionally substituted with one or more hydroxyl groups (e.g. one to six hydroxyl groups).

Examples of such ester-bound (in its widest significance) cross-linked bridges are —O . CO . (CH$_2$)$_{n_1}$ . CO . O—, where $n_1$ is an integer, for example an integer from 1 to 20, preferably 2–10 such as 2–6, and —O . CO . CH$_2$ . O . CH$_2$ . CO . O— and —O . CO . NH . (CH$_2$)$_{n_2}$ . NH . CO . O— and —O . CS . NH . (CH$_2$)$_{n_2}$ . NH . CS . O—, where $n_2$ is an integer, for example an integer from 2 to 6.

In accordance with the invention, the three-dimensional network in question is capable of being degraded by α-amylase in blood plasma into water-soluble fragments, either directly or subsequent to a preceding splitting-off of possibly existing substituents in the polysaccharide under the action of an enzyme in blood plasma, for example, esterases or glucosidases. The degradation of the network by α-amylase takes place owing to the fact that α-amylase hydrolyses glucosidic linkages in the polysaccharide chains of the network. In order that the network should exhibit suitable properties with regard to the degradation of said network by α-amylase, it is generally suitable that the substitution degree of the polysaccharide with respect to the cross-linking bridge substituents and possible occurring singly bound substituents, which cannot be split-off by enzymes in blood plasma, is lower than 70 percent, preferably lower than 60 percent, said substitution degree being given as the percentage of the number of substituted glucose units with respect to the total number of glucose units present. For example, said substitution degree may be lower than 55 percent, e.g. lower than 50 percent. It is generally suitable for the substitution degree of the polysaccharide with respect to the cross-linking bridge substituents and possibly occurring singly bound substituents, which are not capable of being splitoff by enzymes in blood plasma, to be higher than 1 percent, preferably higher than 2 percent, said substitution degree being given as the percentage of the number of substituted glucose units with regard to the total number of glucose units present. For example, the substitution degree may be higher than 5 percent, for example higher than 10 percent. Generally, the substitution degree with respect to all kinds of substituents (i.e. the total substitution degree) is suitably lower than 80 percent preferably lower than 70 percent, for example lower than 60 percent and suitably higher than 1 percent, preferably higher than 2 percent, for example higher than 5 percent. Thus, for example, the substitution degree may be 35 percent, i.e. of 100 glucose units in the polysaccharide chains 35 of these glucose units are carrying at least one substituent.

In accordance with the invention, the cross-linked polysaccharide product is insoluble in water but swellable in water to a gel. It may, for example, contain more than 50 percent by weight of water, such as more than 60 percent by weight of water, preferably more than 65 percent by weight of water, for example more than 70 percent by weight of water. It may, for example contain less than 99.5 percent by weight of water, such as less than 99 percent by weight of water, generally less than 98 percent by weight of water, such as less than 95 percent by weight of water.

In accordance with the invention, the mesh size of the three-dimensional network may be such that protein molecules of the same order of magnitude as α-amylase are able to penetrate into the particles in their water-swollen condition. The mesh size can be determined with the aid of conventional gel chromatographic tests, using substances, such as proteins, of different molecular sizes.

In accordance with the invention, the three-dimensional network of the particles may be such that said network is broken up more slowly by α-amylase in the outer layer of the particle than in the inner part thereof. In this case, the three-dimensional network of the particle may exhibit a higher substitution degree of cross-linking substituents and/or monofunctionally bound substituents in the outer layer of the particle than in the inner part thereof.

The particles may have an irregular shape or may be spherical. Preferably, spherical particles are chosen. The particles have substantially a particle size of the order of 0.1–300 μm (micrometer), generally 1–200 μ, e.g. 1–100 μm in water-swollen state. Preferably the particles in water-swollen state have a size within the range 5–150 μm, for example 10–120 μm. Particles having a size of 5–60 μm in water-swollen state are often chosen for vessels of minor dimensions.

In accordance with the invention, the particle size is selected so that said particles clog fine blood vessels located in or leading to a selected portion of the body, subsequent to being administered intravascularly.

The particle size is selected in dependence upon the dimensions of the blood vessels to be clogged. An example of fine blood vessels of interest in this context is blood capillaries having a diameter of about 5–15 μm and meta-arterioles having a diameter of about 15–300 μm.

One advantageous embodiment of the invention is characterized in that the three-dimensional network can be degraded by α-amylase into water-soluble fragments having substantially a molecular weight beneath 50,000. In this way, the major portion of the fragments are excreted over the kidneys with the urine.

In accordance with the invention, the meshes of the three-dimensional network may be enlarged subsequent to cross-linking by partially degrading said network, e.g. by partial hydrolysis of glucosidic linkages in the cross-linked polysaccharide chains. Such a partial hydrolysis may be effected, for example, with an acid or α-amylase.

In accordance with the invention, subsequent to being injected into the blood vessels, the particles can be degraded into water-soluble fragments by α-amylase within, for example, the space of some few seconds to many hours, depending upon the effect desired in each individual case. With regard to the particles according to the invention, the degradation time may thus be varied within wide limits and can be well and reproducably established for the desired field of use.

The cross-linking of the polysaccharide molecules to a practically infinite three-dimensional network can be effected by reacting the polysaccharide or the polysaccharide derivative in question with an at least bifunctional cross-linking agent. Preferably, the cross-linking agent is reacted with hydroxyl groups in the polysaccharide chains whereby many bridges of the following type are obtained between the polysaccharide chains: $P_1 — O — B — O — P_2$, wherein $— B —$ is a bridge-forming link between oxygen atoms derived from hydroxyl groups in two different polysaccharide chains $P_1$ and $P_2$. Preferably, the bridge-forming link B contains at least 3 carbon atoms, for example 3–30 carbon atoms or 3–20 carbon atoms.

For the purpose of obtaining cross-linking bridges which are bound to the polysaccharide chains over ether bonds, the polysaccharide or the polysaccharide derivative can be reacted for example, in an alkaline aqueous solution with a cross-linking agent, for example of the type:

$$X . A_1 . Z \qquad (I)$$
and
$$\begin{array}{c} Y \\ . \\ X . A_2 . Z \end{array} \qquad (II)$$

where X, Y and Z each represent a halogen atom, preferably chloro or bromo and $A_1$ and $A_2$ each represent a straight or branched aliphatic, saturated hydrocarbon chain which is substituted by one or more hydroxyl groups (e.g. one to six) and which preferably contains 3–30 carbon atoms, for example 3–20 carbon atoms, such as 3–10 carbon atoms and which is optionally broken by one or more oxygen atoms (e.g. one to six), or with a corresponding epoxide compound which can be obtained from the the compound (I) or (II) by splitting off hydrogen halide. Examples of bifunctional substances of the formula $X . A_1 . Z$ and corresponding epoxide compounds which can be obtained from compounds of said formula by splitting off hydrogen halide are:

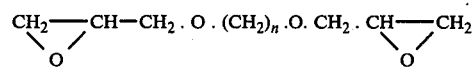

where n is an integer, for example from 2 to 4 and

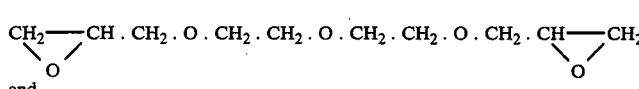
and
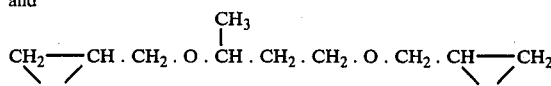
and
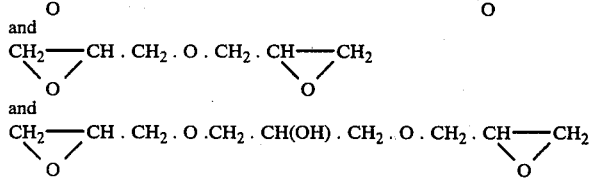

or a corresponding halogen hydrins, and bifunctional glycerol derivatives of the formula X . CH$_2$ . CH(OH) . CH$_2$ . Z, for example, dichlorohydrin and dibromohydrin, or corresponding epoxide compound (obtainable by splitting off hydrogen halide) of the formula

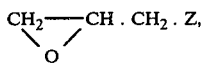

e.g. epichlorohydrin or epibromohyrin. Another example of such a bifunctional compound is 1,2- 3,4-diepoxybutane of the formula

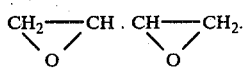

An example of a trifunctional cross-linking agent (which is an epoxide compound corresponding to a compound of the formula

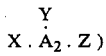

is

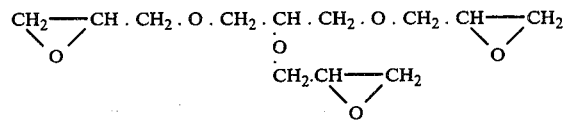

The polysaccharide or the polysaccharide derivative is reacted with such a quantity of an at least bifunctional cross-linking agent that a water-insoluble gel is formed, i.e. a practically infinite three-dimensional network which exhibits the desired properties. One skilled in this art can readily establish empirically a suitable relationship between the quantities of different polysaccharides or polysaccharide derivatives and cross-linking agent.

For the purpose of obtaining cross-linking bridges which are bound to the polysaccharide chains over ester bonds, the polysaccharide or the polysaccharide derivative can be reacted in a manner known per se with, for example, aliphatic or heterocyclic or aromatic dicarboxylic acids or reactive derivatives thereof, e.g. with dicarboxylic acid dichlorides (e.g. of succinic acid or of adipic acid) or for example, with diisocyanates or diisothiocyanates. Other cross-linking agents may also be used.

The cross-linking reaction, in addition to bridge-building, also often results in the introduction of monofunctionally bound (i.e. singly bound) substituents (mono-ethers, mono-esters etc.) from the cross-linking agent, i.e. only one reactive group in the at least bifunctional bridge-building agent has reacted with a hydroxyl group in a polysaccharide chain whilst the other reactive group or groups in the bridge-forming agent have e.g. instead reacted with, e.g. water to form, e.g. hydroxyl groups or carboxyl groups, etc. Consequently, the polymer product most frequently presents also monofunctionally bound substituents originating from the bridge-building agent; e.g. —O . CH$_2$ . CH(OH) . CH$_2$OH when the bridge-building agent is epichlorohydrin, and —O . CH$_2$ . CH(OH) . CH$_2$ . O . (CH$_2$)$_4$ . O . CH$_2$ . CH(OH) . CH$_2$OH when the bridge-building agent is 1,4-butandiol-diglycideether or, e.g. —O . CO . (CH$_2$)$_{n_1}$ . COOH when the bridge-building agent is a dicarboxylic acid dichloride.

The polymeric gel product can be obtained in particle form ether by producing the polymer in the form of large pieces (bulk polymerisation) and then disintegrating said product, e.g. by grinding, or by producing the product by bead polymerisation techniques in the form of spherical particles. In this latter case, the reaction mixture is dispersed to droplet form in an inert liquid which is immiscible therewith, whereafter the gel particles formed by the reaction in the droplets are recovered. Particles having a spherical shape are preferably used. The desired particle size can be obtained by fractionating the particles, e.g. by screening the same.

The gel product obtained can be substituted with different groups, e.g. for controlling the rate with which the particles are degraded by α-amylase in blood plasma. For this purpose, hydroxyl groups in the polysaccharide chains may be substituted with substituents, e.g. of the aforementioned type such as lower alkyl, lower carboxyalkyl, lower hydroxyalkyl and/or lower alkanoyl. The substituents may, for example, be ether bound and/or ester bound to the polysaccharide chains.

For the purpose of controlling the rate of degradation of the gel particles in blood plasma, the particles can be subjected to partial hydrolysis in vitro (e.g. with an acid or with α-amylase) prior to or during the preparation of the suspension. This partial hydrolysis of glucosidic linkages is continued until the gel particles have obtained the desired properties.

The agent according to the invention can be injected intravasculary when it is desired to block blood vessels located in or leading to a part of the body. A blocking of blood vessels for a shorter or longer period of time is of interest in many experimental procedures but also in diagnostic or therapeutic procedures. As an example it can be mentioned that the particle suspension according to the invention is very useful for blocking blood vessels located in or leading to a cancer tissue in a specific portion of the body, whereby the blood flow to the cancer tissue can be stopped or reduced which can lead to inhibition or reduction of the growth of the cancer tissue or even to reduction or disappearing of the tumor mass. (This effect can be increased if the particle suspension is administered intravascularly in conjunction with other cancer therapy.) For this special purpose, the particles in water-swollen state may, for example, have a size in the order of 5–150 μm, preferably 10–120 μm.

The diagnostic agents or therapeutic agents or therapeutic agents which may be used in conjunction with the agent are preferably such agents which can be administered intravasculary.

The diagnostic agent may advantageously comprise an X-ray contrast agent. The X-ray contrast agent will often be an agent which is soluble in water. This agent may be dissolved in a physiologically acceptable aqueous liquid. Normally the conventional iodine-containing, water-soluble contrast agents are used, although it is possible to use any contrast agent which is intravascularly acceptable. The water-soluble contrast agents are often physiologically acceptable salts (e.g. sodium salts and methyl glucamine salts) of 2,4,6-triiodo bensoic acid derivatives, such as 3,5-bisacetylamino-2,4,6-triiodo bensoic acid, 3-acetylamino-5-acetylmethylamino-2,4,6-triiodo bensoic acid and 5-acetylamino-2,4,6-triiodo-N-methyl-isophthalic acid-monoamide. Other examples of suitable iodine-containing contrast agents are described in Swedish Patent Specifications Nos. 344,166, 348,110 and 348,111. The contrast agent may also be a non-ionic contrast agent.

The diagnostic agent may, for example, also be a radioactive substance. This substance may be in solution or in the form of minute particles (optionally on an inorganic or an organic carrier material), the radioactive particles being in general of the same size as, or smaller than the agent particles based on polysaccharide. A large number of such agents containing radioactive isotopes for the before-mentioned purpose are known to the art. The radioactive isotope may be an isotope of e.g. an inert gas, such as xenon or krypton, or may be a substance which contains a radioactive isotope of e.g. iodine or phosphorous, e.g. sodium iodide or sodium phosphate, or a substance which contains radioactive technetium, for example sodium pertechnetate (used as such or reduced with e.g. stannous chloride), or a substance which contains a radioactive isotope of chromium, indium, gold, yttrium, ytterbium, cerium, cobalt, carbon or hydrogen. Two or more different radioactive isotopes may also be used. The concentration and radioactivity of the radioactive substance or substances used is such as to enable the diagnosis in question to be carried out.

The therapeutic agent may, for example, be a cytostatically acting agent, for example an agent for the treatment of cancer, such as cyclophosphamide and similar substances or a radioactive substance. It may, for example, also be a substance which affects the blood vessels or which affects coagulation, or a substance which affects the formation or dissolution of thrombosis, or an antimicrobial substance or an antiinflammatory substance, or an anaesthetic or a substance exhibiting a hormone effect, or an antiparasitic substance.

A mixture of two or more diagnostic and/or therapeutic agents may also be used.

The agent and the diagnostic agent or the therapeutic agent are administered in doses of a magnitude which enables the desired effect to be obtained in each individual case. In general, the quantity of the agent administered (calculated for each individual) corresponds to 0.1 to 2,000 mg particles, e.g. 0.5 to 200 mg particles, and is dependent upon e.g. the examination or the therapy to be carried out, e.g. the region of blood vessels to be blocked. The quantity may be in the region of from 0.001 mg to 50 mg, preferably 0.01 mg to 25 mg, for example 0.05 mg to 10 mg particles per kilo body weight.

The concentration of the particles in the suspension may be varied within wide limits, depending upon the purpose of use. For example, it may be more than 0.01 mg, e.g. more than 0.1 mg, such as more than 1 mg particles per 1 ml suspension, e.g. less than 200 mg, e.g. less than 50 mg, such as less than 25 mg particles per 1 ml suspension. The physiologically acceptable aqueous liquid in which the particles are suspended may comprise liquids normal for intravascular injection, e.g. physiological sodium chloride solution (i.e. 0.9% aqueous solution of NaCl) or aqueous solutions of the salts occurring in the blood plasma. Glucose, sorbitol or saccharose solutions may also be used in some cases, e.g. 5–10% aqueous solutions thereof.

An agent or composition according to the invention is prepared by suspending the particles described above in a physiologically acceptable aqueous liquid. The amount of particles and the amount of liquid are chosen so that the desired concentration of particles in the liquid is obtained. For example, the amount of particles per 1 ml suspension can be chosen within the ranges given above. One or more therapeutic or diagnostic agents or other physiologically acceptable substances such as intravascularly acceptable additives for regulating the stability and/or viscosity and/or density and/or the osmotic pressure of the suspension may be added when preparing the suspension. Preferably, the suspension is made isotonic with conventional such additives, for example with NaCl, glucose or sorbitol. The suspension can be filled in bottles (e.g. containing 1–1000 ml suspension) which may be sealed.

Preferably, sterile suspensions of the particles are used. Sterilization can be effected by heat treatment, e.g. autoclaving, or by adding substances which prevent the growth of microorganisms. The suspensions may also be prepared aseptically.

The agent is intended to be administered intravascularly (i.e. preferably in blood vessels, although it may also be administered, for example, in lymph vessels) preferably in conjunction with (i.e. simultaneously or almost at the same time as) an intravascular administration of a solution or a suspension of an intravascularly acceptable diagnostic or therapeutic agent. Thus, the agent may be administered intravascularly immediately prior to, simultaneously as or immediately subsequent to the intravascular administration of the diagnostic or therapeutic agent, depending upon the effect desired in each separate case. In general, the agent is administered some few seconds before or after the intravascular administration of the diagnostic or therapeutic agent or simultaneously therewith. In certain cases, for example when the agent is administered prior to the administration of said diagnostic or therapeutic agent, a relatively large time difference may be employed, for example a time difference of 10 to 30 seconds, and in particular cases of some minutes or still longer periods of time.

Subsequent to being administered intravascularly, the particles of the agent block the finer blood vessels, thereby to cause the flow of blood in the vessels to be impeded, so that the residence time of the diagnostic or the therapeutic agent in the vessel system is prolonged or the passage travelled by said agent redirected. When the agent is administered at the same time as the diagnostic or the therapeutic agent, the agent particles and the diagnostic or therapeutic agent are preferably held in the same region of the blood vessels and preferably upstream of the finest vessels.

When the agent is administered intravascularly immediately subsequent to administering the diagnostic or the therapeutic agent, the diagnostic or the therapeutic agent may have passed the finest vessels, which are then blocked by the agent particles, whereupon the diagnostic or therapeutic agent is wholly or partially held in the vessel bed downstream of the finer vessels as seen in the flow direction, e.g. in the veinside of the vessel system.

When the agent is administered intravascularly before administering the diagnostic or the therapeutic agent, the diagnostic or the therapeutic agent may be held in vessel portions upstream of the finer vessels which are blocked by the agent particles, or may be totally excluded from the relevant vessel portion. In this way it is possible also to redirect the flow paths of the diagnostic or the therapeutic agent.

By means of the present invention it is possible to satisfactorily fill a vessel system or a portion of a vessel with a diagnostic agent or a therapeutic agent with a prolonged retention time of said agents in said vessel portion or system in question, in a manner which is free from risk, owing to the favourable properties of the particles, inter alia the soft gel consistency of the particles, and owing to the fact that the three-dimensional network of said particles is water-swollen and that the rate at which the particles are degraded enzymatically into water-soluble fragments, can be varied in reproducable and determinable manner, which can be controlled precisely both in vitro and in vivo. (This is in contrast to previously known particles, including albumin microspheres, which are digested irregularly mainly by phagocytosis in vivo. Currently used albumin particles are not significantly digested in cell-free body fluids.)

When the diagnostic agent is an X-ray contrast agent, it is possible, for example, to effect an angiography of the blood vessels on both the artery side and the vein side, whereby it is possible to obtain good and detailed X-ray pictures of the vessel system in question. This enables vessels to be visibilized which otherwise could not be photographed with X-rays, or at least only with difficulty. When administering the particles first, it is also possible to shut off a vessel area so that the X-ray contrast agent is unable to enter said region but remains in the coarse vessels leading to said region, which coarse vessels can be visibilized, and/or is redirected to other vessels which can be visibilized. Thus, the invention affords both new and improved X-ray diagnostic possibilities.

Similarly, improved and new diagnostic results can be obtained when the diagnostic agent is a radioactive substance.

As a result of the agent, it is possible to treat defined portions of the body of a patient with therapeutic substances. The therapeutic agent may, for example, be any one of the before-mentioned substances, such as a cytostatically acting substance for the treatment of cancer.

In accordance with the invention the agent may be in mixture with a diagnostic agent. The diagnostic agent may, advantageously, be an X-ray contrast agent. The X-ray contrast agent is often a water-soluble X-ray contrast agent. This agent may be dissolved in the physiologically acceptable aqueous liquid in the suspension. Normally, the conventional iodine-containing water-soluble contrast agents are used, although, as will be readily understood, any intravascularly acceptable contrast agent may be used. The water-soluble contrast agent may, for example, comprise one or more of the before-mentioned agents. They may be present, for example, in quantities such that the iodine content of the suspension is from 100 to 400 mg I/ml, e.g. 200–350 mg I/ml. The diagnostic agent, with which the agent is in mixture, may also comprise, for example, one or more radioactive agents, for example one or more of the before-mentioned substances. In this instance the concentration of the diagnostic agent in the mixture is sufficient to enable the diagnosis in question to be carried out.

In accordance with the invention the agent may also be in mixture with a therapeutic agent. This may, for example, be a cytostatically active substance or any one of the before-mentioned agents.

A preferred embodiment of the agent according to the invention is a composition for intravascular administration, which composition comprises a sterile suspension of minute particles in a physiologically acceptable aqueous liquid, optionally in combination with one or more therapeutic or diagnostic agents and optionally in combination with intravascularly acceptable additives for regulating the stability and/or viscosity and/or density and/or the osmotic pressure of the suspension, said particles having a size in water-swollen state within the range 5–150 μm comprising a polysaccharide built up of glucose units or a physiologically acceptable derivative of said polysaccharide, said polysaccharide or polysaccharide derivative being cross-linked to a water-insoluble, hydrophilic, swellable, three-dimensional network of molecules of the polysaccharide or of the derivative thereof by means of bridges (a) having bonds of a covalent nature and (b) being bound to the molecules of the polysaccharide or of the derivative thereof over ether bonds and/or ester bonds and (c) containing 3–30 carbon atoms, which network can be broken by α-amylase in blood plasma into water-soluble fragments, either directly or subsequent to a preceding splitting off of possibly occurring substituents, preferably glucoside-bound and/or ester-bound substituents, in the polysaccharide by the action of an enzyme, preferably glucosidase and/or esterase, in blood plasma, the content of swelled particles in the suspension corresponding to more than 0.01 mg and to less than 200 mg dry particles per 1 ml suspension.

The invention also relates to an auxiliary agent for use in the preparation of the relevant agent or composition for intravascular administration, comprising minute particles which comprise a polysaccharide built up of glucose units or physiologically acceptable derivative of said polysaccharide, the particles having a size such that, subsequent to being administered intravascularly, they block the finer vessels located in or leading to a portion of the body. The auxiliary agent according to the invention is characterized in that the particles comprise a water-insoluble but hydrophilic, swellable, three-dimensional network of molecules of the polysaccharide or the derivative thereof cross-linked by means of bridges having bonds of a covalent nature, which network is capable of being broken by α-amylase in blood plasma into water-soluble fragments, either directly or subsequent to a preceding splitting off of possibly occurring substituents, preferably glucoside-bound and/or ester-bound substituents, in the polysaccharide by the action of an enzyme, preferably gluclosidase and/or esterase, in blood plasma.

The disclosures made in the aforegoing with respect to the minute particles in conjunction with the agent also apply to the particles of the auxiliary agent.

The invention also relates to a method of effecting a diagnosis by the intravascular administration of a solution or a suspension of a diagnostic agent in a blood vessel located in or leading to a specific portion of the body, wherewith in conjunction with said administration there is also administered intravascularly an agent which consists of or contains a suspension of minute particles, comprising a polysaccharide built up of glucose units or a physiologically acceptable derivative of said polysaccharide in a physiologically acceptable aqueous liquid, the size of the particles being such that subsequent to being administered intravascularly said particles block the finer vessels located in or leading to said body portion, the diagnosis being effected with the aid of the diagnostic agent. The method according to the invention is characterized in that the particles comprise a water-insoluble but hydrophilic, swellable, three-dimensional network of molecules of the polysaccharide or of the derivative thereof cross-linked by means of bridges having bonds of a covalent nature, wherein the network can be broken by α-amylase in blood plasma into water-soluble fragments, either directly or subsequent to a preceding splitting-off of possibly occurring substituents, preferably glucoside-bound and/or ester-bound substituents, in the polysaccharide by the action of an enzyme, preferably glucosidase and/or esterase, in blood plasma. The disclosures made in the aforegoing with respect to the minute particles in conjunction with the agent also apply with respect to the particles etc. in conjunction with the method of effecting a diagnosis.

Particularly favourable results are obtained with the method according to the invention when the diagnostic agent is an X-ray contrast agent. Preferably, a water-soluble X-ray contrast agent is selected which can be administered dissolved in a physiologically acceptable aqueous liquid, the diagnosis being effected by X-ray examination. When so desired, the water-soluble X-ray contrast agent can be dissolved in the physiologically acceptable aqueous liquid in the suspension, the diagnosis being effected by X-ray examination.

With the method of the invention, the diagnostic agent may also favourably be, for example, a radioactive agent, such as one of the previously mentioned agents.

The term "body" as applied here and in the claims relates to the body of animals having blood vessels, especially mammals including man.

EXAMPLE 1

333 g of soluble starch having a molecular weight ($\overline{M}_w$) of approximately 20,000 were dissolved in 533 ml of water containing 53 g of sodium hydroxide and 2 g of sodium borohydride. Subsequent to being stirred for 4 hours, the solution was allowed to stand for 2 days with a layer of octanol on the surface thereof (about 0.5 ml). A clear solution was obtained.

In a cylindrical reaction vessel provided with a thermometer, a cooler and agitator there were dissolved 20 g of Gafac® PE 510 (a complex organic phosphoric acid ester which served as an emulsion stabilizer and which is obtainable from General Aniline Film Corp.) in 1 liter of ethylene dichloride at room temperature, whereafter the previously prepared starch solution was added. The mixture was stirred at a speed such that the water phase was dispersed to droplet form of the desired magnitude in the ethylene dichloride phase. The size of the droplets formed upon agitation of the starch suspension in ethylene dichloride was controlled with the aid of a microscope. After adjusting the speed of the agitator to 1100 rpm, which gave an average droplet size of 70 $\mu$m, 40 g of epichlorohydrin were added.

After a reaction time of 16 hours at 50° C., the product was poured into 5 liters of acetone and allowed to settle. The supernatent liquid was drawn off and the product was slurried in 5 liters of acetone. The acetone was drawn off, 8 liters of water were added and the pH adjusted to 5, by adding acetic acid. The product was then slurried a further four times in 8 liters of water and 5 times in 5 liters of acetone, whereafter the product was dried in vacuum at 50° C. for 2 days, The product weighed 241 g.

The polymer particles were insoluble in water but swelled in water to gel form, the gel particles containing 83 percent by weight of water. The degree of substitution was about 35%.

Part of the product was suspended well in water. The suspension was then screened by water-streaming on screens having a mesh size of 100 $\mu$m, 80 $\mu$m, 56 $\mu$m, 40 $\mu$m and 25 $\mu$m. The particles remained on the different screens in accordance with the following weight distribution (the weight are given in dry weight):

| Mesh size in /$\mu$m | weight (g) |
|---|---|
| 80 | 7.9 |
| 56 | 45 |
| 40 | 4.9 |
| 25 | 11.2 |

The fractions were washed with distilled water, and were then washed free of water with acetone and dried in a vacuum at 50° C. for 2 days.

EXAMPLE 2

With respect to products prepared in the manner disclosed in Example 1 but with varying quantities of epichlorohydrin, the effect of the quantities of epichlorohydrin used, on the degradation of the particles by means of $\alpha$-amylase was examined in the following manner:

7 mg of particles having a size which, when wet-screening the particles in accordance with Example 1, passed through a screen having a mesh size of 40 $\mu$m but which remained on a screen having a mesh size of 25 $\mu$m, were weighed in a polypropylene vessel and slurried in 20 ml of 0.05 M sodium phosphate buffer, pH 7, with 0.05% Tween ® 20 (wetting agent) (polyoxyethylene-sorbitan-monolaurate from Atlas Chemie GmbH). The beaker was placed under agitation in a bath, the temperature of which was adjusted to 37° C. When the temperature had stabilized, there were added 200 $\mu$l of $\alpha$-amylase from swine pancreas from a stock solution having a concentration of 150,000 IE/l or 24,000 IE/l (IE = international units). 500 $\mu$l of sample were pipetted at uniform intervals down in Ellerman tubes containing 2 ml of an 1 percent aqueous sodium hydroxide solution, whereafter the tubes were centrifuged for 5 minutes. One ml of the supernatant was then pipetted over to a plastic tube, for determining the quantity of substance which, as a result of the effect of the $\alpha$-amylase, had been released from the particles and had passed into solution.

As a measurement of the rate of degradation, the time was recorded in which half of the mass of the particles was refound in the supernatant. The following result was obtained:

| Epichlorohydrin (quantity in grams) | Water content of swelled particle (% weight) | Degree of substitution (in %) | Time (min) with 240 IE $\alpha$-amylase/1 | Time (min) with 1500 IE $\alpha$-amylase/1 |
|---|---|---|---|---|
| 20 | ~96 | | <5 | <3 |
| 25 | 93 | ~20 | 19 | 8 |
| 30 | 85 | 29 | 26 | 8.5 |
| 40 | 83 | 36 | 38 | 15.5 |
| 45 | 80 | 40 | 50 | 21 |
| 50 | 76 | 42 | 73 | 30 |
| 60 | 74 | | | 62 |

When the amount of epichlorohydrin was 60 g, only 25% of the mass of the particles passed into solution in two hours with 240 IE $\alpha$-amylase/l.

EXAMPLE 3

1.0 g of dry particles produced in accordance with Example 1 but at an agitator speed of 1500 rpm and having a size which, when wet-screened, passed through a screen having a mesh size of 40 $\mu$m but remained on a screen having a mesh size of 25 μm, were swollen in 30 ml of water. 0.4 g of acetic acid anhydride dissolved in 5 ml of tetrahydrofuran was added dropwise to the particle suspension over a period of 10 minutes (the pH being kept at 8.5–9 by addition of 1 M aqueous NaOH solution), whereafter the suspension was neutralized. The gel grains were then washed with distilled water and acetone, and then dried. The water-swollen particles contained approximately 85% by weight of water. The total degree of substitution was about 50%.

Hydrolysis with 0.1 N sodium hydroxide and titration with 0.1 N hydrochloric acid gave 1.51 mmol of acetyl per gram of dry product. When degrading with α-amylase in accordance with the method described in Example 2, half of the mass of the particles were found in the supernatant after 6 hours with 240 IE α-amylase per liter and after 1 hour and 9 minutes with 1500 IE α-amylase per liter, respectively. For the unsubstituted starting product, half of the mass of the particles was found in the supernatant after 40 minutes with 240 IE α-amylase per liter and after 15 min with 1500 IE α-amylase per liter, respectively. Thus, the substitution with acetyl groups had considerably increased the degradation time in the presence of α-amylase in vitro.

EXAMPLE 4

84 g of carboxymethyl starch having a substitution degree of 20% and a molecular weight ($\overline{M}_w$) of about 20,000 were dissolved in 38 ml of water containing 13.7 g of sodium hydroxide and 0.05 g of sodium borohydride. Subsequent to being agitated for 4 hours, the solution was allowed to stand for 2 days with a layer of octanol on the surface thereof (some few drops). A clear solution was obtained.

In a cylindrical reaction vessel provided with a thermometer, a cooler, and an agitator, there were dissolved 20 g of Gafac ® PE 510 (a complex organic phosphoric acid ester which serves as an emulsion stabilizer) in 265 ml of ethylene dichloride at room temperature, whereafter the previously prepared starch solution was added. The mixture was agitated at a speed such that the water phase dispersed to droplets of the desired size in the ethylene dichloride phase. The size of the droplets formed in the starch suspension in ethylene dichloride upon said agitation was controlled with the aid of a microscope. Subsequent to adjusting the agitating speed to 1500 rpm, 10.3 g of epichlorohydrin were added.

After 18 hours reaction time at 50° C. the product was poured in 2 liters of acetone and allowed to settle. The supernatant was drawn off and the product slurried in 2 liters of acetone. The acetone was drawn off, 2 liters of water were added and the pH adjusted to 5 with acetic acid. The product was slurried four times with distilled water admixed with 0.5 g of sodium azide, and five times with 1250 ml of acetone, whereafter the product was dried in vacuum at 60° C. for 2 days. The product weighed 69 g. The particles were insoluble in water but swelled in water to gel particles, the particles containing about 90% by weight of water. When degraded with α-amylase in accordance with the method described in Example 2, half of the mass of the particles was found in the supernatant after 4.5 and 2.5 hours respectively with α-amylase content 240 and 1500 IE/l respectively.

EXAMPLE 5

2 g of dry particles were prepared in the manner described in Example 1, but with an agitating speed of 330 rpm and swollen particle size which passed through a screen having a mesh size of 125 μm but which remained on the screen having a mesh size of 100 μm. The particles were stirred in 25 ml of 0.1 M hydrochloric acid at 20° C. A sample amounting to about 0.3 g of particles was taken at different intervals of time, said samples being centrifuged and washed with distilled water three times and treated with acetone and dried in a vacuum at 50° C. for 16 hours. The time taken for half the mass to degrade to water-soluble fragments under the action of α-amylase as described in Example 2 was then determined. The following results were obtained:

| Time for hydrochloric acid treatment (hours) | Degradation time (min) with 1500 IE α-amylase/l |
| --- | --- |
| 0 | 60 |
| 3 | 52 |
| 6 | 33 |
| 19 | 8 |

EXAMPLE 6

16 g of a dry product prepared in accordance with Example 1 having a particle size which, when wet-screened, passed through a screen having a mesh size of 40 μm but which remained on a screen having a mesh size of 25 μm, were swollen and suspended in 400 ml of distilled water. 0.85 g of propylene oxide was added and the pH adjusted to 12 with 2 M sodium hydroxide. The suspension was maintained at 50° C. and agitated for 24 hours, whereafter the suspension was neutralized with acetic acid, washed with water and wet-screened with water. The fraction which passed through the screen having a mesh size of 40 μm but which remained on a screen having a mesh size of 25 μm was recovered. 2.5 g product was obtained. The product was insoluble in water but swelled in water to gel particles, said particles containing approximately 80% by weight of water. The total degree of substitution was 40%.

EXAMPLE 7

An experiment was carried out in the manner disclosed in Example 1, but instead of epichlorohydrin, there were added 90 g of 1,4-butandioldiglycidyl ether and the speed of the agitator was maintained at 1400 rpm, which resulted in an average droplet size of 25 μm. In other respects the experimental conditions were the same as those disclosed with reference to Example 1 and washing and drying were also effected in the manner disclosed in Example 1. 294 g of product were obtained.

The product was insoluble in water, but swelled in water to gel particles, the particles containing about 75% by weight water. (The degree of substitution was estimated to be about 40%.)

10 g of the product were suspended in about 200 ml of water and were subjected to an ultrasonic treatment process. The suspension was then screened by water-screening through screens having mesh sizes of 56 μm, 40 μm and 25 μm. The particles remained on the different screens in accordance with the following weight distribution (the weights are given as dry weight):

| Mesh size (μm) | weight (g) |
| --- | --- |
| 40 | 2.8 |
| 25 | 4.2 |

The fractions were washed with distilled water and acetone, whereafter they were dried.

EXAMPLE 8

33 g of hydroxyethyl starch having a molecular weight ($\overline{M}_w$) of about 143,000, were dissolved in 54 ml of water containing 5.3 g of sodium hydroxide and 0.2 g of sodium borohydride. Subsequent to a clear solution being formed there were added 2 g of Gafac ® PE 510 dissolved in 100 ml of ethylene dichloride and the mixture was agitated at a speed such that a suspension of droplets having an average diameter of 50 μm was formed. 4 g of epichlorohydrin were then added and the mixture was stirred for 16 hours at 50° C. The product was poured into acetone and allowed to settle. The acetone was decanted and the product swollen in water. The pH was adjusted to 5 with HCl, whereafter the product was washed with distilled water, acetone and petroleum ether.

The product was then dried at 50° C. in vacuum. The product weighed 33.6 g and presented a substitution degree of about 66%. The water-insoluble product swelled in water to gel particle form, the particles containing about 75% by weight of water. 10 g of the product were screened on screens having a mesh size of 80 μm, 56 μm, 40 μm and 25 μm by water screening. The particles remained on the different screen in accordance with the following weight distribution (dry weight):

| Mesh size (μm) | weight (g) |
| --- | --- |
| 80 | 3.9 |
| 56 | 1.5 |
| 40 | 0.9 |
| 25 | 1.5 |

EXAMPLE 9.

90 mg of dry particles were prepared in accordance with Example 2 with 25 g of epichlorohydrin and a size which, when the particles were wet-screened, passed through a screen having a mesh of 40 μm but remained on a screen having a mesh size of 25 μm, were suspended in 6 ml of a 0.9% NaCl-solution.

10 ml of an X-ray contrast agent Isopaque ® Coronar (i.e. an aqueous solution of contrast agent which per ml contained 101 mg sodium metrizoate, 656 mg methyl glucamine metrizoate and 11.3 mg calcium metrizoate having an iodine content corresponding to 370 mg I/ml from Nyegaard & Co A/S, Norway) were injected into the liver artery of an anaesthetized dog (weighing approximately 20 kg) for the purpose of visibilizing the blood vessels of the liver by X-ray photography.

After some hours, the above prepared suspension of particles in 0.9% NaCl-solution was injected into the liver artery. Immediately hereafter (within the space of 5 seconds) 10 ml of Isopaque Coronar were injected. X-ray pictures were taken during the test. In this instance only the coarse vessel were visibilized; the finer vessels were not seen owing to the fact that these were blocked by the particles which prevented the contrast solution from entering thereinto. In this way there was obtained an angiogram of the coarser vessels freed from the background of finer vessels filled with contrast agent.

EXAMPLE 10

3 ml of the X-ray contrast agent Conray ® Meglumin (i.e. an aqueous solution of contrast agent which contains per ml 600 mg of methyl glucamine iodothalamate having an iodine content corresponding to 280 mg I/ml from Astra-Meditec AB) were injected into the left kidney artery of an anaesthetized dog (weighing approximately 19 kg) for the purpose of visibilizing the blood vessels of the kidney by X-ray photography.

After some hours a further 3 ml of Conray ® Meglumin were injected into the same kidney artery. Immediately subsequent hereto (within the space of a few seconds) a suspension of 45 mg of particles prepared according to Example 1 (having a swollen average size of 40 μm) in 3 ml of 0.9% aqueous solution of NaCl were also injected. X-ray pictures were taken during the test. In this case finer blood vessels were visibilized on the X-ray pictures than in the before-mentioned comparison test without the injection of particles. The blood vessels were also visible for a longer period of time than with the comparison test. In addition the blood vessels on the vein side were visibilized in a much more advantageous manner, owing to the fact that the small blood vessels were blocked immediately after administering the contrast agent when the contrast agent was located on the vein side of the blood vessels.

EXAMPLE 11

A catheter was inserted in an anaesthetized dog weighing 27 kg from the right artery femoralis to the artery mesenterica. 70 mg of particles prepared in accordance with Example 1 and having a swollen size which, when wet screened, passed through a screen having a mesh size of 56 μm but remained on a screen having a mesh size of 40 μm, and suspended in 10 ml of the X-ray contrast agent Urografin ® 60% (i.e. water-dissolved mixture of sodium and methyl glucamine salts of $N_1N^1$-diacetyl-3,5-diamino-2,4,6-triiodo bensoic acid in the ratio of 10:66 having an iodine content corresponding to 290 mg I/ml, from Schering AG, West Germany) were then injected into the dog. X-ray pictures (angiographs) were taken in conjunction with the injection. The blood vessels of the intestines were clearly visibilized (i.e. the vessels which are served by the artery in question) down to the prearteriol level. The contrast effect was maintained during the whole of the X-ray picture series, which is not the case with the comparison tests without particles. Far thinner blood vessels were seen than with conventional angiography. The effect remained for several minutes. A check was made after 40 minutes, when it was found that the flow conditions were again normal, this being established with conventional angiography without particles.

EXAMPLE 12

A dog weighing 33.5kg was anaesthetized. The liver artery of the dog was then administered twice with 0.5 ml of 133-Xe-solution (activity 0.8 mCi/ml). In both cases there were obtained satisfactory exponential curves over the activity in the liver region as a function of time, where the slopes of the curves were identical. When the activity had disappeared, 20 ml particle suspension (300 mg of particles prepared in accordance with Example 1 having a swollen average size of 25–40 μm, suspended in 20 ml of a 0.9% NaCl aquoues solution) were injected. This suspension was injected approximately 3–5 seconds after an injection of the Xe-solution. Subsequent hereto a curve having a much smaller incline was obtained. Initially, however, the Xe-peak was smaller owing to the fact that the activity of the Xe-solution had decreased. The time when the activity of the injected Xe-solution had decreased to half (i.e. $T\frac{1}{2}$) was read from the curves. A measurement of the residence time of the Xe-solution ($K = 1n2/T\frac{1}{2}$) was then calculated from the obtained value of $T\frac{1}{2}$.

It was found hereby that the mean value of $T\frac{1}{2}$ was 0.37 minutes and that the mean value for $K$ was 1.95 in the first two tests. In the case of the test in which the particle suspension was injected after the Xe-solution the values obtained with respect to $T\frac{1}{2}$ and $K$ were 1.50 minutes and 0.45 respectively. This implies that the residence time of the Xe-solution was increased by 424%, by injecting the particle suspension.

EXAMPLE 13

Particles were prepared in the manner described in Example 1, but with an agitating speed of 330 rpm and a water-swollen particle size which passed through a screen having a mesh size of 100 μm but which remained on a screen having a mesh size of 80 μm. The water content of the swelled particles and the degree of substitution were the same as in Example 1. 15 grams of the dried particles were suspended well in 1000 ml of 0.9% aqueous NaCl solution. The suspension was filled in 25 ml bottles which were sealed and sterilized by autoclaving.

A catheter was introduced into the liver artery of a patient (weight about 70 kg) who had large metastasis in the right liver lobe. The tumour was visibilized with conventional X-ray investigations. The tumour had a diameter of about 11 cm. 25 ml of the particle suspension were injected daily for ten days into the liver artery through the catheter. After the last injection new X-ray investigations were made. The tumour had now a diameter of about 4 cm, i.e. a considerable reduction of the size of the tumour. After 4 months a new investigation of the patient was made. There was now no general sign of malignancy and on the tumour site in the liver only a small calcified area was now seen.

With similar procedures several other patients having tumours have been injected intravascularly with the same particle suspension into blood vessels leading to the cancer tissue region also in conjunction with therapy with cytostatic agents with successful results.

What is claimed is:

1. In the known method of effecting a diagnosis by the intravascular administration of a solution or a suspension of a diagnostic agent in an amount effective for said diagnosis, said diagnostic agent being selected from the group consisting of X-ray contrast agents for intravascular use and radioactive diagnostic agents for intravascular administration in a blood vessel located in or leading to a restricted portion of the body, in which method in conjunction with said administration there is also administered intravascularly an agent which comprises minute particles suspended in a physiologically acceptable aqueous liquid, said particles in water-swollen state having a size such that subsequent to being intravascularly administered they block the finer blood vessels located in or leading to the said body portion, and said minute particles being administered in an amount effective for blocking said blood vessels, said diagnosis being effected with the aid of the diagnostic agent, the improvement which comprises using as said minute particles a three-dimensional, water-insoluble, hydrophilic, swellable, cross-linked network of polysaccharide substances, said network being composed of
a polysaccharide substance selected from the group consisting of starch, amylose, amylopectin, glycogen and dextrins thereof,
cross-linking having been effected by ether bonds that form bridges between polysaccharide substances, said bridges being straight or branched aliphatic saturated hydrocarbon chains substituted with one to six hydroxyl groups and containing 3–20 carbon atoms and being unbroken or broken with one to six oxygen atoms,
said three-dimensional network being degradable by the α-amylase in blood plasma into water-soluble fragments.

2. In the known method of effecting a diagnosis by the intravascular administration of a solution or a suspension of a diagnostic agent in an amount effective for said diagnosis, said diagnostic agent being selected from the group consisting of X-ray contrast agents for intravascular administration in a blood vessel located in or leading to a restricted portion of the body, in which method in conjunction with said administration there is also administered intravascularly an agent which comprises minute particles suspended in a physiologically acceptable aqueous liquid, said particles in water-swollen state having a size such that subsequent to being intravascularly administered they block the finer blood vessels located in or leading to the said body portion, and said minute particles being administered in an amount effective for blocking said blood vessels, said giadnosis being effected with the aid of the diagnostic agent, the improvement which comprises using as said minute particles a three-dimensional water-insoluble hydrophilic, swellable, cross-linked network of polysaccharide substances, said network being composed of:
a polysaccharide substance selected from the group consisting of starch, amylose, amylopectin, glycogen and dextrins thereof, or a physiologically acceptable derivative of one of the aforesaid polysaccharides, said derivative containing as substituents at least one member selected from the group consisting of 2-hydroxyethyl, 2-hydroxypropyl, 2,3-dihydroxypropyl, acethyl, propionyl, 2-hydroxypropanoyl, succinoyl and glutaroyl,
cross-linking having been effected by ether bonds that form bridges between polysaccharides substances, said bridges being straight or branched aliphatic saturated hydrocarbon chains substituted with one to six hydroxyl groups and containing 3–20 carbon atoms and being unbroken or broken with one to six oxygen atoms,
said three-dimensional network being degradable by the α-amylase in blood plasma into water-soluble fragments.

3. A method according to claim 2 wherein the total substitution degree for the polysaccharide is lower than 70%, said substitution degree being given as the percentage of the number of substituted glucose units with respect to the total number of glucose units present.

4. A method according to claim 2 wherein the total substitution degree of the polysaccharide is lower than 60%, said substitution degree being given as the percentage of the number of substituted glucose units with respect to the total number of glucose units present.

5. A method according to claim 2 wherein said cross-linked polysaccharide substance swells to a gel in the presence of water, said gel containing more than 60% by weight of water.

6. A method according to claim 2 wherein said cross-linked polysaccharide substance swells to a gel in the presence of water, said gel containing more than 65% by weight of water.

7. A method according to claim 2 wherein the meshes of said three-dimensional network have a size such that protein molecules of the same size as α-amylase are able to penetrate into the particles in their water-swollen state.

8. A method according to claim 2 wherein the outer layer of said three-dimensional network is degraded more slowly by α-amylase than the central portion of said network.

9. A method according to claim 2 wherein said particles are substantially spherical in shape.

10. A method according to claim 2 wherein said particles have a size of 5–150 μm in their water-swollen state.

11. A method according to claim 2 wherein said three-dimensional network can be degraded by α-amylase into water-soluble fragments having a molecular weight beneath 50,000.

12. A method according to claim 2, wherein said particles are administered in the form of a sterile suspension thereof in a physiologically acceptable aqueous liquid in combination with intravascularly acceptable additives for regulating at least one property selected from the group consisting of the stability, viscosity, density and osmotic pressure of the suspension.

13. A method according to claim 12, wherein said particles have a size within the range of 5–150 μm in their water-swollen state and wherein the content of swelled particles in the suspension corresponds to more than 0.01 mg and to less than 200 mg of dry particles per 1 ml suspension.

14. A method according to claim 2 wherein said diagnostic agent is a water-soluble X-ray contrast agent for intravascular use, which is administered dissolved in a physiologically acceptable aqueous liquid and wherein the diagnosis is effected by X-ray examination.

15. A method according to claim 2 wherein the diagnostic agent is a water-solution X-ray contrast agent for intravascular use dissolved in the physiologically acceptable aqueous liquid in the suspension and wherein the diagnosis is effected by X-ray examination.

16. In the known method of blocking fine blood vessels by administering intravascularly into said vessel an agent comprising minute particles suspended in a physiologically acceptable aqueous liquid, said particles in water-swollen state having a size such that subsequent to being intravascularly administered they block said fine block vessels and said minute particles being administered in an amount effective for blocking said blood vessels, the improvement which comprises using as said minute particles a three-dimensional water-insoluble hydrophilic, swellable, cross-linked network of polysaccharide substances, said network being composed of a polysaccharide substance selected from the group consisting of starch, amylose, amylopectin, glycogen and dextrins thereof, cross-linking having been effected by ether bonds that form bridges between polysaccharide substances, said bridges being straight or branched aliphatic saturated hydrocarbon chains substituted with one to six hydroxyl groups and containing 3–20 carbon atoms and being unbroken or broken with one to six oxygen atoms, said three-dimensional network being degradable by the α-amylase in blood plasma into water-soluble fragments.

17. In the known method of blocking fine blood vessels, by administering intravascularly into said vessels an agent comprising minute particles suspended in a physiologically acceptable aqueous liquid, said particles in water-swollen state having a size such that subsequent to being intravascularly administered they block said fine blood vessels, and said minute particles being administered in an amount effective for blocking said blood vessels, the improvement which comprises using as said minute particles a three-dimensional water-insoluble hydrophilic, swellable, cross-linked network of polysaccharide substances said network being composed of a polysaccharide substance selected from the group consisting of starch, amylose, amylopectin, glycogen and dextrins thereof or a physiologically acceptable derivative of one of the aforesaid polysaccharides, said derivative containing as substituents at least one member selected from the group consisting of 2-hydroxyethyl,2-hydroxypropyl, 2,3-dihydroxypropyl, acetyl, propionyl, 2-hydroxypropanoyl, succinoyl and glutaroyl, cross-linking having been effected by ether bonds that form bridges between polysaccharide substances, said bridges being straight or branched aliphatic saturated hydrocarbon chains substituted with one to six hydroxyl groups and containing 3–20 carbon atoms and being unbroken or broken with one to six oxygen atoms, said three-dimensional network being degradable by the α-amylase in blood plasma into water-soluble fragments.

18. A method according to claim 17, wherein the total substitution degree for the polysaccharide is lower than 70%, said substitution degree being given as the percentage of the number of substituted glucose units with respect to the total number of glucose units present.

19. A method according to claim 17 wherein the total substitution degree of the polysaccharide is lower than 60%, said substitution degree being given as the percentage of the number of substituted glucose units with respect to the total number of glucose units present.

20. A method according to claim 17 wherein said cross-linked polysaccharide substance swells to a gel in the presence of water, said gel containing more than 60% by weight of water.

21. A method according to claim 17 wherein said cross-linked polysaccharide substance swells to a gel in the presence of water, said gel containing more than 65% by weight of water.

22. A method according to claim 17 wherein the meshes of said three-dimensional network have a size such that protein molecules of the same size as α-amylase are able to penetrate into the particles in their water-swollen state.

23. A method according to claim 17 wherein the outer layer of said three-dimensional network is degraded more slowly by α-amylase than the central portion of said network.

24. A method according to claim 17 wherein said particles are substantially spherical in shape.

25. A method according to claim 17 wherein said particles have a size of 5–150 μm in their water-swollen state.

26. A method according to claim 17 wherein said three-dimensional network can be degraded by α-amylase into water-soluble fragments having a molecular weight beneath 50,000.

27. A method according to claim 17 wherein said particles are administered in the form of a sterile suspension thereof in a physiologically acceptable aqueous liquid in combination with intravascularly acceptable additives for regulating at least one property selected from the group consisting of the stability, viscosity, density and osmotic pressure of the suspension.

28. A method according to claim 27 wherein said particles have a size within the range of 5–150 μm in their water-swollen state and wherein the content of swelled particles in the suspension corresponds to more than 0.01 mg and to less than 200 mg of dry particles per 1 ml suspension.

29. A method according to claim 17 wherein said fine blood vessels are located in or leading to a cancer tissue.

* * * * *